(12) United States Patent
Amundsen et al.

(10) Patent No.: US 8,779,362 B1
(45) Date of Patent: Jul. 15, 2014

(54) INFRARED ACID DETECTOR AND METHOD

(76) Inventors: Ted J. Amundsen, Melbourne, FL (US); David C. Hahn, Rockledge, FL (US)

( * ) Notice: Subject to any disclaimer, the term of this patent is extended or adjusted under 35 U.S.C. 154(b) by 275 days.

(21) Appl. No.: 13/447,327

(22) Filed: Apr. 16, 2012

(51) Int. Cl.
*G01N 21/35* (2014.01)

(52) U.S. Cl.
USPC ............................. 250/339.13; 250/339.01

(58) Field of Classification Search
CPC  G01N 21/35; G01N 21/3504; G01N 21/3554
USPC .......... 250/338.1, 338.5, 339.01, 339.13, 343
See application file for complete search history.

(56) References Cited

U.S. PATENT DOCUMENTS

| | | |
|---|---|---|
| 3,739,260 A | 6/1973 | Schadler |
| 4,488,118 A | 12/1984 | Jeffers et al. |
| 4,923,806 A | 5/1990 | Klodowski |
| 5,071,768 A | 12/1991 | Klodowski |
| 5,377,496 A | 1/1995 | Otto et al. |
| 6,791,088 B1 | 9/2004 | Williams, II et al. |
| 7,253,413 B2 | 8/2007 | Sauer et al. |
| 2008/0092648 A1* | 4/2008 | Zhou et al. ................. 73/335.01 |

* cited by examiner

*Primary Examiner* — Mark R Gaworecki

(57) ABSTRACT

A method and apparatus for detecting the presence and concentration of organic and inorganic acids by their infrared absorption characteristics in a refrigeration unit while running. Acids of interest, such of those formed upon decomposition of refrigerant or refrigerant oil, are volatilized and subjected to infrared radiation. Optical filtering is used to limit the infrared radiation to relevant wavelengths. Organic acids are detected by the absorbance of energy between 4-6 microns while inorganic acids are detected by the absorbance of energy between 2-4 microns.

14 Claims, 3 Drawing Sheets

INFRARED ACID DETECTOR AND METHOD

BACKGROUND AND SUMMARY OF THE INVENTION

The present invention is in the technical field of acid detection. More particularly, the present invention is in the technical field of acid detection in vapor compression heating, air conditioning, and refrigeration systems, and is an electronic acid detector and method that uses infrared absorbance to determine the type and concentration of acid in a system as well as to detect moisture.

Vapor compression refrigerators, heat pumps, and air conditioners must always be concerned with the presence of acids in the refrigerant which can severely shorten the life of both the compressor and refrigerant. These acids can be formed by chemical reactions of the refrigerant or refrigeration oil with moisture, components and/or materials of construction, and/or impurities. The instabilities of the refrigerants and refrigeration oils are accelerated by elevated temperatures which result from improper operation, such as a failed condenser fan, or clogged air flow path.

Checking the refrigerant and/or oil acid is a common maintenance procedure because acidic compounds can be cleaned up before permanent damage to the hardware and refrigerant occur. Acids in a refrigeration system can potentially result in hermetic compressor motor burn-out because the acid will degrade the motor winding's electrical insulation, causing an electrical short. Acids in a refrigeration system can also form high-viscosity sludge which does not provide adequate lubrication and can also clog the expansion device. The presence of acid indicates the existence of other decomposition products, such as non-condensable gases, which result in elevated pressures leading to reduced efficiency and overloaded compressor operation.

To avoid the above-mentioned problems, refrigeration systems are tested for acid content. Typically, the oil would be tested for acid, because the highest concentration of acid is found in the oil of a non-operating system (shut down). It is, however, much easier to test the system for acid while operational. Several indicator systems are known for testing the presence and concentration of contaminants in a refrigerant. For example, U.S. Pat. Nos. 4,923,806 and 5,071,768 show apparatuses for testing liquid or vapor contaminants in a closed system whether the apparatus is operating or not. A disposable testing tube made of transparent material is used at the end of a compressor discharge line or elsewhere in the system. One section of the tube is provided with water removal and moisture indicating chemicals, such as cobaltus chloride and another section is provided with acid indicating chemicals such as a solution of bromophenol blue, ethanol, and glycerol. This construction is relatively complicated and requires a separate, specially configured flow restrictor in addition to a tube holder, and an expensive testing tube in which the multiple contaminant testing chemicals and filter screens are located.

Likewise, U.S. Pat. No. 5,377,496 shows an acid contamination indicator for closed loop vapor compression systems in which the indicator is permanently or removably installed in the bypass line around the system compressor where the refrigerant is always in the gaseous phase. A casing has a visual indicator bed of bromophenol blue as the acid indicating medium which is contacted by the refrigerant after flowing through a filter and a flow restrictor orifice. Porous retainer discs are held against the bed by springs. The solid indicator must be mixed with an inert substance to provide some porosity, contact surface area, and increased volume and then packaged in a clear tube. Again, we have recognized that this is an unduly complicated construction which requires a substantial outlay for installation.

Another type of contaminant detector is marketed by Refrigeration Technologies of Fullerton, Calif. under the trademark "CHECKMATE". A specific volume of gas passes through a detection tube at a predetermined termination pressure. However, an expensive sealed Pyrex detection tube containing a color-changing chemical and whose ends are pierced when fully assembled can only be used once even when the test is negative, and thus this approach entails considerable expense regardless of its technical merits. These systems were also developed to detect inorganic mineral acids, which are highly corrosive and therefore easier to detect. With the new refrigerants and oils, mild organic acids are typically formed. These acids which can lead to slug formation, are more difficult to detect.

Electronic refrigerant leak detectors operate on a variety of principles including heated diodes as in U.S. Pat. No. 3,739,260, negative corona discharge as in U.S. Pat. No. 4,488,118, and infrared (IR) absorbance as in U.S. Pat. No. 6,791,088. The method disclosed in the latter patent can be summarized thusly: After the IR signal is detected electrically, it is filtered through a band pass filter and then amplified. The signal is then sent through an accumulator/peak detector with a large capacitor to store small signals for a longer period of time; it then is passed into a subtracting op-amp to remove any zero offset set by the potentiometer. The signal is then further processed and delivered to the user as feedback via a lighted display indicating leak intensity. However, no prior art instrument has recognized or addressed the detection of acids as well as moisture in an HVAC/R system using IR detection methods.

Infrared absorbance has been used to monitor the presence of a large variety of gases, including acids. This technology is described in U.S. Pat. No. 7,253,413 and has been commercialized by Smiths Detection Inc. as the "GasID" portable gas and vapor chemical identifier. This device is used for the identification of flammables, corrosives, toxic industrial chemicals, and weapons of mass destruction. The system uses a pump to deliver the gaseous sample to an adsorbent bed where the sample can be concentrated for full-spectrum IR analysis. An attached computer then processes the spectral data and a graphical user interface conveys information such as chemical identification to the operator. The gas is sampled for approximately 10 minutes before matches are communicated to the operator. This apparatus is too complicated, expensive, and slow to be used as a portable hand-held device for the portable detection of acids in an HVAC/R system located in the field.

BRIEF DESCRIPTION OF THE DRAWINGS

The features, objects and advantages of the present invention will become readily apparent from the following detailed description thereof when taken in conjunction with the accompanying drawings wherein.

DETAILED DESCRIPTION OF THE DRAWINGS

While organic acids are too dilute in the vapor phase to be detected by conventional methods such as known colorimetric indicators, a device measuring IR absorbance has been discovered to detect accurately even low concentrations of volatilized organic acids in an HVAC/R system. The acids are detected by monitoring the absorption of energy with wavelengths specific to the acids of interest. Optical filtering is used to limit the infrared radiation to relevant wavelengths. Organic acids are detected by the absorbance of energy between 4-8 microns while inorganic acids are detected by the absorbance of energy between 3-4 microns. This method can also be used to measure the moisture content in the system by absorbance of energy between 3-5 microns. Of course, the IR spectra for water is different from that of acid and can thus be distinguished.

Figure 1:
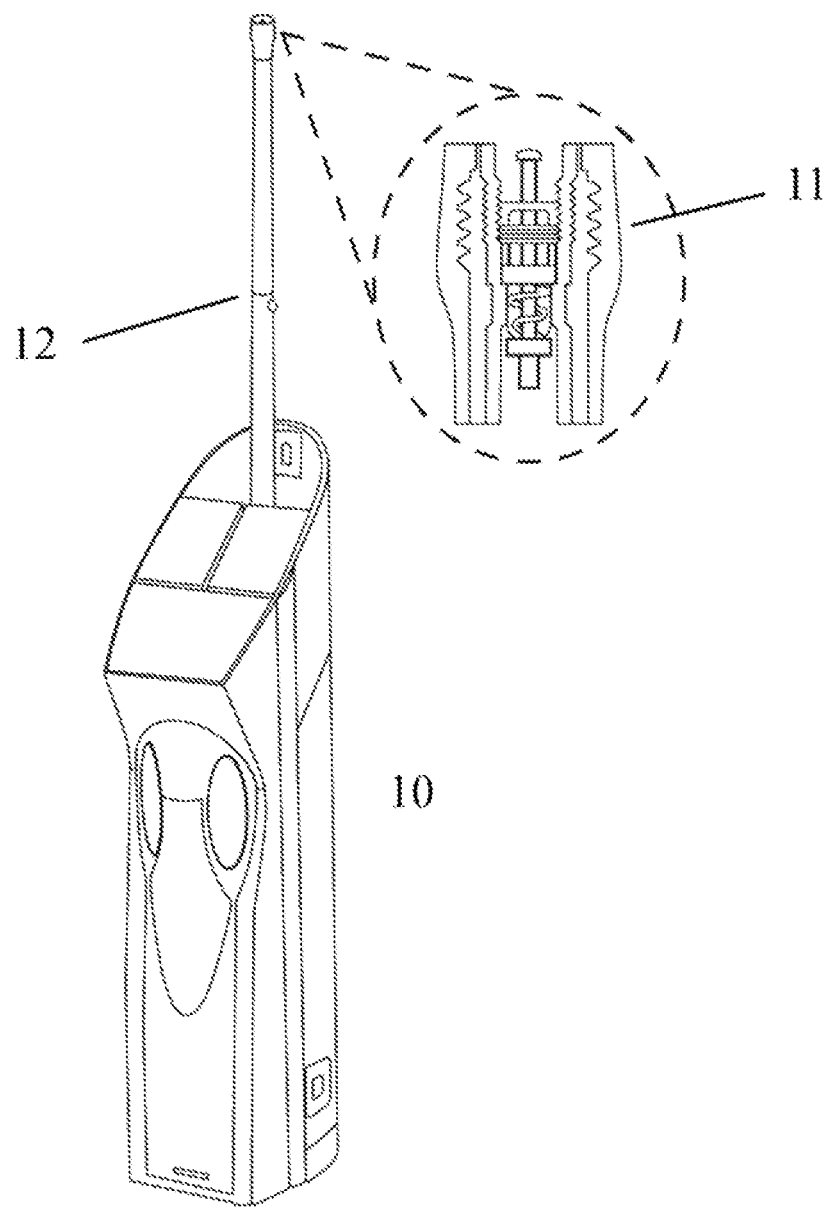
FIG. 1 is a perspective view showing the IR-based multi-mode acid, moisture, and/or leak detector in accordance with the present invention.

Our infrared acid detector designated generally by the numeral 10 in FIG. 1 has a response time on the order of seconds and is able to detect acids in a refrigeration unit while running. It is important to note that the present invention can not only detect acids, but can distinguish between organic and inorganic acids. This is important because the common system failure method for systems containing inorganic acid is a compressor burn-out, while the common system failure for a system containing organic acids is sludge formation, and the treatment methods for organic and inorganic acids are different.

The detector of the present invention can be powered by battery or by an electrical power cord. It can be either a portable, handheld unit or permanently installed as an in-line sensor to monitor refrigerant and oil acid formation. The currently preferred embodiment of our detector 10 shown in FIG. 1 is a multi-functional handheld IR instrument capable of detecting acids as well as refrigerant leaks. The detector may use an air pump for sampling to improve detection limits and allow detection at a greater distance from the source. The refrigerant vapors can be analyzed in an open system by venting a small portion of the refrigerant vapors from the high pressure service valve or in a closed loop for greater sensitivity.

The apparatus can include an IR emitter or emitters, IR beam filters, an IR detector or detectors, and a sample collection chamber where the gaseous sample is subjected to IR radiation and detection. The IR beam may be continuous so that it operates by detecting a change in acid concentration from baseline when put into contact with the test sample.

Figure 2:
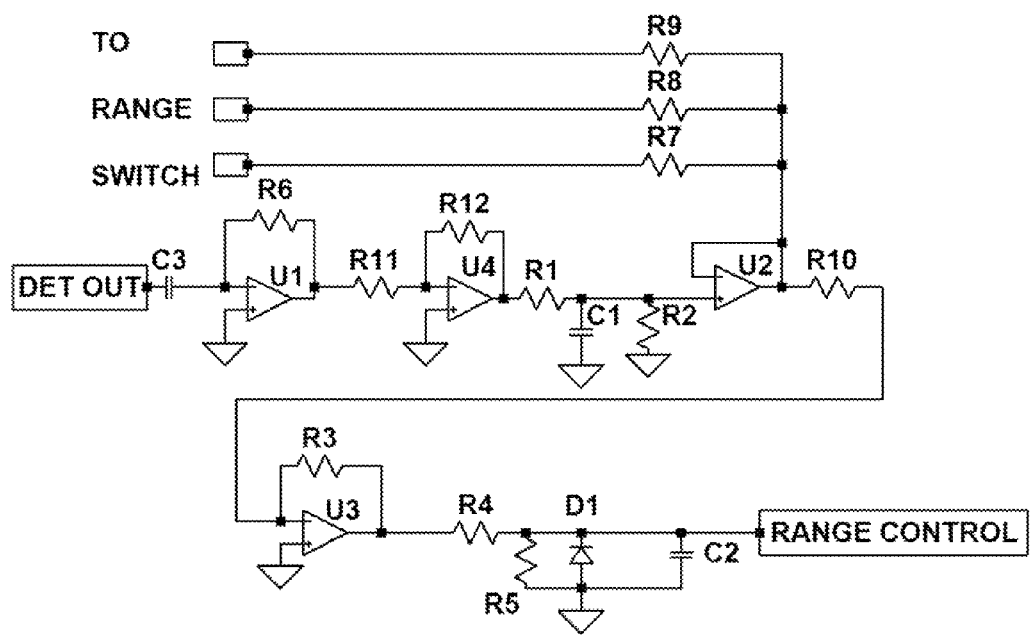
FIG. 2 is a schematic diagram showing the signal conditioning circuit with automatic offset adjustment used in the detector of FIG. 1 in accordance with the present invention.

Electrically, the infrared acid detection method of the present invention is similar to the method used to detect refrigerant leaks as disclosed in the above-mentioned U.S. Pat. No. 6,791,088, and thus the disclosure of said patent as regards refrigerant leak detection is incorporated herein by reference. In this connection. FIG. 2 of the present application uses the same numerals used in FIG. 6b of said U.S. Pat. No. 6,791,088 to designate common parts having identical functionality. We have discovered, however, that this known leak detection approach can also be used to detect the presence of acid and water in a system, and the detection of the type of acid in a system so as to provide a single instrument with multiple functionalities.

In order to provide these additional functionalities and to simplify ease of use, we have found that the offset adjustment potentiometer functionality in said U.S. Pat. No. 6,791,088 can be removed by replacing the subtractor (designated as U8:A in FIG. 6b of the U.S. Pat. No. 6,791,088 incorporated by reference herein and the surrounding resistors R57, R56, R31, and R67 and adjustment potentiometer R46) with, as shown in FIG. 2 of the present application, a differentiator comprised of U1, R6, and C3. An inverting amplifier comprised of U4, R11, and R12 is included to compensate for the differentiator's negative gain. The differentiator will take the derivative of the signal from the accumulator and remove any DC offset. Because a derivative is taken, a constant background level will output no signal, while a constantly rising value (implying a leak) will output a constant signal proportional to the rate of rise. Thus, the user no longer sets a zero level depending on the background amount present as the differentiator automatically performs this task, reducing complexity and simplifying operation for the user. A filter may also be used to protect the IR cell from oil droplets and other contaminants. This filter may be constructed of a variety of materials including carbon, inorganic oxide, and/or polymer.

In leak detection mode, the instrument can be swept along the lines and joints of an HVAC/R system to determine the location of the leak by detecting the IR spectra for a refrigerant in the manner described in said U.S. Pat. No. 6,791,088. The intensity of the response will increase as the detector gets closer to the leak, allowing the operator to precisely locate the location of a leak.

In acid or moisture detection mode, the detector 10 can be placed outside the service valve (Schrader-valve) to sample the gaseous refrigerant/oil mixture when the valve core is depressed. The tip 11 of the detector 10 may be outfitted with a generally known structure (shown enlarged in the isolated section in dashed lines) capable of depressing the service valve so that refrigerant may flow to the detector for analysis. The tip 11 may reside at the end of an extendable telescoping appendage 12 to provide a rigid base so that enough force can be applied to the service valve in order to depress the valve core. This will allow analysis of the gas at a standardized distance as well as a safe method of opening the service valve.

Figure 3:
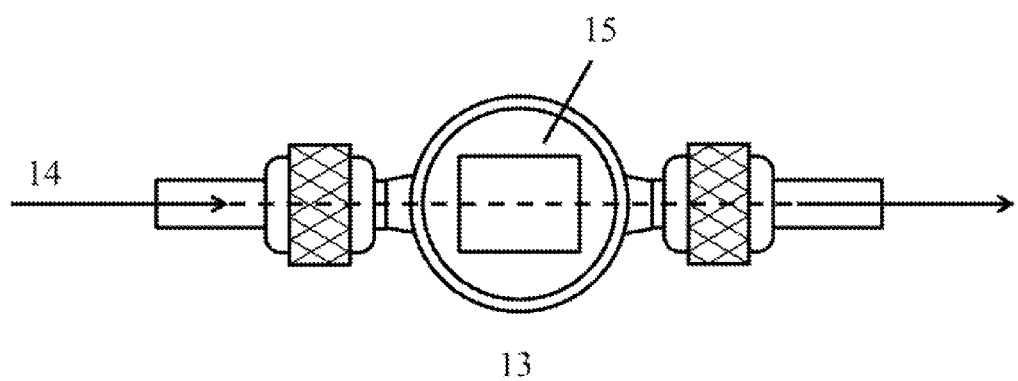
FIG. 3 is a plan view showing an in-line IR-based multi-mode acid and moisture sensor in accordance with the present invention.

In another contemplated embodiment, the acid/moisture detector can be an in-line monitoring system which measures the acid and/or moisture content of the operating system using the same IR absorbance method as the handheld device. This device is shown generally in FIG. 3 as numeral 13. The gaseous refrigerant 14 along with any entrained contaminants enters the device where it is analyzed. The refrigerant then exits the sensor and reenters the system. A visual and/or aural indicator 15 alerts the operator to the presence of acid or moisture. This device can either be affixed in-line with the refrigerant flow in the system or in a by-pass line connected between high pressure and low pressure service ports of the system.

Advantages of the present invention include, without limitation, the ability to detect acids in an HVAC/R system with a handheld electronic instrument or in-line sensor. In addition to detecting refrigerant leaks similar to the method disclosed in above-discussed U.S. Pat. No. 6,791,088, our invention can also be used to detect the presence of acid and water in a system, and the detection of the type of acid in a system. Combining all these features in a single handheld instrument provides greater value to the equipment operator. The instrument is reusable and is able to detect acids in a refrigeration system while operating. Further, both inorganic and organic acids formed from both refrigerant and oil breakdown are detected and distinguished by this apparatus.

While the foregoing written description of the invention enables one of ordinary skill to make and use what is considered presently to be the best mode contemplated, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the appended claims.

We claim:

1. A method of detecting at least one of inorganic acid and organic acid in a vapor compression system, comprising sampling refrigerant vapor contained in the system, subjecting the sampled refrigerant vapor to an infrared beam, and observing infrared absorbance of the sampled refrigerant vapor to detect a presence of the at least one of inorganic acid and organic acid.

2. The method of claim 1, wherein the observed absorbance is compared in the 4-8 micron range for detecting organic acids.

3. The method of claim 1, wherein the observed absorbance is compared in the 3-4 micron range for detecting inorganic acids.

4. The method of claim 1, wherein the observed absorbance is compared in the 3-5 micron range for optionally detecting moisture.

5. The method of claim 1, wherein the sampling is effected by venting the refrigerant from a service valve through a sensor in the device and into ambient air.

6. The method of claim 1, wherein the sampling is obtained with a portable hand-held device.

7. The method of claim 1, wherein the sampling is undertaken by locating a sensor in-line with refrigerant flow in the system.

8. The method of claim 1, wherein the sampling is undertaken by locating a sensor in a by-pass line connected between high pressure and low pressure service ports of the system.

9. The method of claim 1, wherein the infrared beam is one of a pulsed beam and a continuous beam.

10. The method of claim 1, wherein the sampling is undertaken during operation of the system.

11. The method of claim 1, wherein the subjecting of the sampled refrigerant vapor comprises performing optical filtering to maintain the infrared beam at a desired wavelength.

12. A portable handheld device for detecting at least one of inorganic acid and organic acid in a vapor compression system, comprising a tip for obtaining a sample of refrigerant vapor contained in the system, a sampling chamber, an infrared beam having a desired wavelength for subjecting the sample to testing, and circuitry configured to measure an infrared absorbance of the subjected sample containing at least one of inorganic acid and organic acid in the sampling chamber.

13. The device of claim 12, wherein the circuitry is configured to measure the sample absorbance in the 3-4 micron range for inorganic acid detection, the 4-8 micron range for organic acid detection and in the 3-5 micron range for optional moisture detection.

14. The device of claim 12, wherein an optical filter is provided to obtain the desired wavelength.

* * * * *